(12) United States Patent
Greenwald et al.

(10) Patent No.: US 6,360,115 B1
(45) Date of Patent: *Mar. 19, 2002

(54) SYSTEM FOR IMAGING MECHANICALLY STABILIZED TISSUE

(75) Inventors: Roger J. Greenwald, Holley, NY (US); Milind Rajadhyaksha, Charlestown, MA (US)

(73) Assignees: Lucid, Inc., Rochester, NY (US); The General Hospital Corp., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/397,329

(22) Filed: Sep. 16, 1999

Related U.S. Application Data

(63) Continuation of application No. 08/912,331, filed on Aug. 18, 1997, now Pat. No. 5,978,695.

(51) Int. Cl.[7] .............................................. A61B 5/05
(52) U.S. Cl. ...................................... 600/407; 600/476
(58) Field of Search .............................. 600/407, 415, 600/425, 587, 417, 421, 429, 473, 476; 378/37, 62, 63, 195; 128/915

(56) References Cited

U.S. PATENT DOCUMENTS

| | | |
|---|---|---|
| 4,212,306 A | 7/1980 | Mahmud |
| 4,774,961 A | 10/1988 | Carr |
| 4,829,184 A | 5/1989 | Nelson et al. |
| 5,034,613 A | 7/1991 | Denk et al. |
| 5,056,523 A | 10/1991 | Hotchkiss, Jr. et al. |
| 5,064,429 A | 11/1991 | Waterman et al. |
| 5,349,954 A | 9/1994 | Tiemann et al. |
| 5,371,368 A | 12/1994 | Alfano et al. |
| 5,524,636 A | 6/1996 | Sarvazyan et al. |
| 5,595,177 A | 1/1997 | Mena et al. |
| 5,730,133 A | 3/1998 | Godik |
| 5,772,597 A | 6/1998 | Goldberger et al. |
| 5,788,634 A | 8/1998 | Suda et al. |
| 5,807,261 A | 9/1998 | Benaron et al. |
| 5,820,552 A | 10/1998 | Crosby et al. |
| 5,833,612 A | 11/1998 | Eckhouse et al. |
| 5,833,633 A | 11/1998 | Sarvazyan |
| 5,836,877 A | 11/1998 | Zavislan |
| 5,978,695 A * | 11/1999 | Greenwald et al. ......... 600/407 |
| 5,995,283 A * | 11/1999 | Anderson et al. ........... 359/385 |
| 5,999,836 A * | 12/1999 | Nelson et al. .............. 600/407 |
| 6,243,484 B1 * | 6/2001 | Godik ......................... 382/128 |

OTHER PUBLICATIONS

Rajadhyaksha et al., "In Vivo Confocal Scanning Laser Microscopy of Human Skin: Melanin Provides Strong Contrast", The Journal of Investigative Dermatology, vol. 104, No. 6, Jun. 1995, pp. 1–7.

Rajadhyaksha et al., "Confocal laser microscope images tissue in vivo", Laser Focus World, Feb. 1997, pp. 119–127.

Kesterson et al., "Confocal Microscope Capability with Desktop Affordability", Advanced Imaging, Oct. 1991 pp. 23–24.

Schmitt et al., "Optical characterization of dense tissues using low–coherence interferometry", SPIE, vol. 1889, pp. 197–211 (1993).

* cited by examiner

*Primary Examiner*—Brian L. Casler
(74) *Attorney, Agent, or Firm*—Kenneth J. LuKacher

(57) ABSTRACT

A system is provided having a clamping apparatus with first and second members, which are spaced apart from each other. An attachment mechanism is connected to the first member for attaching the apparatus to a confocal imaging system. This attachment mechanism has a surface with a window facing the tissue to be examined. Opposing this surface is a third member connected to the second member. A clamping mechanism includes the first and second members for clamping the tissue between the surface of the attachment mechanism and the surface of the third member, thereby stabilizing the tissue to the confocal imaging system. The window of the attachment mechanism presents the clamped tissue to the confocal imaging system.

8 Claims, 9 Drawing Sheets

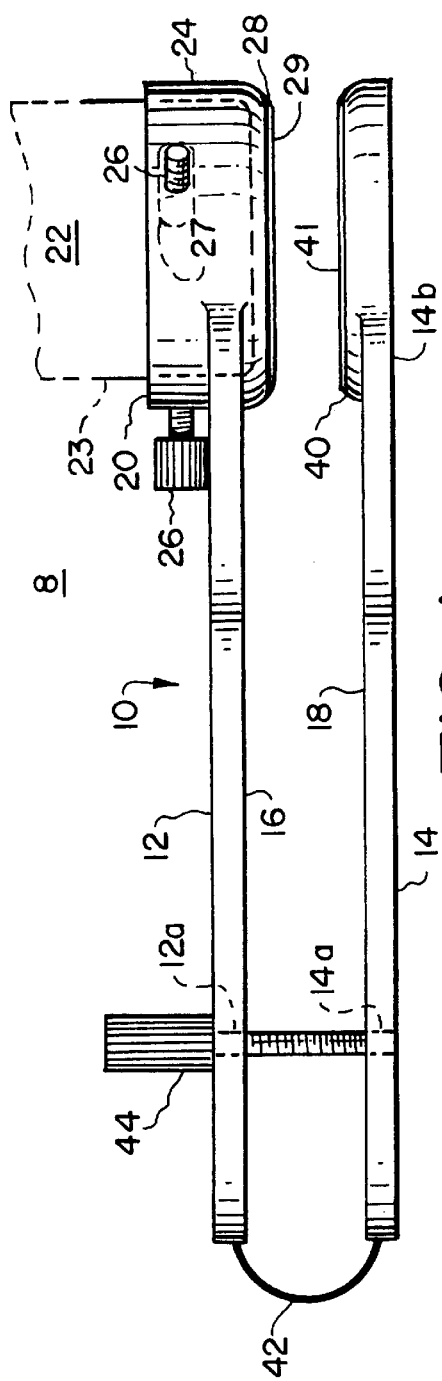
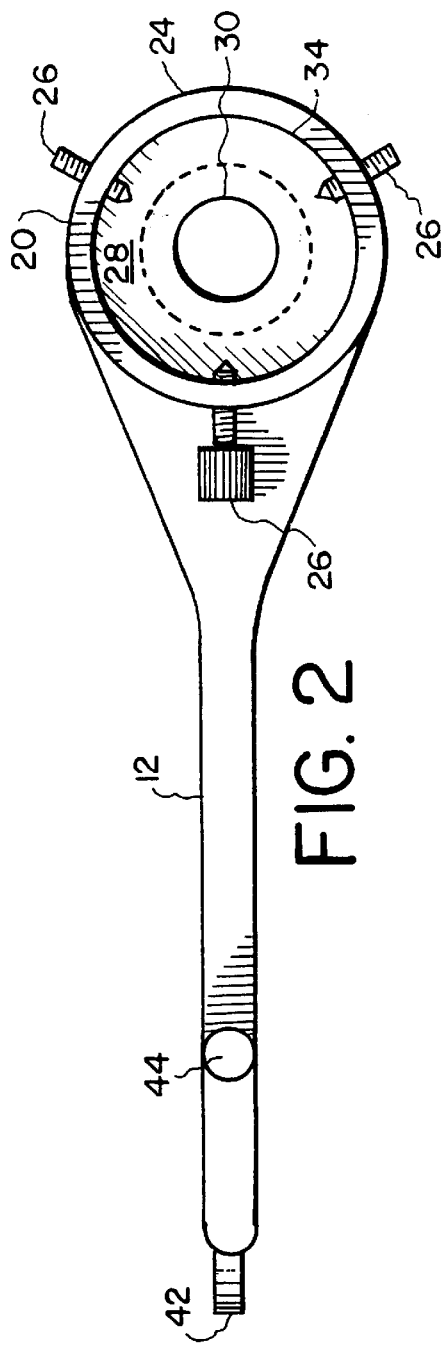

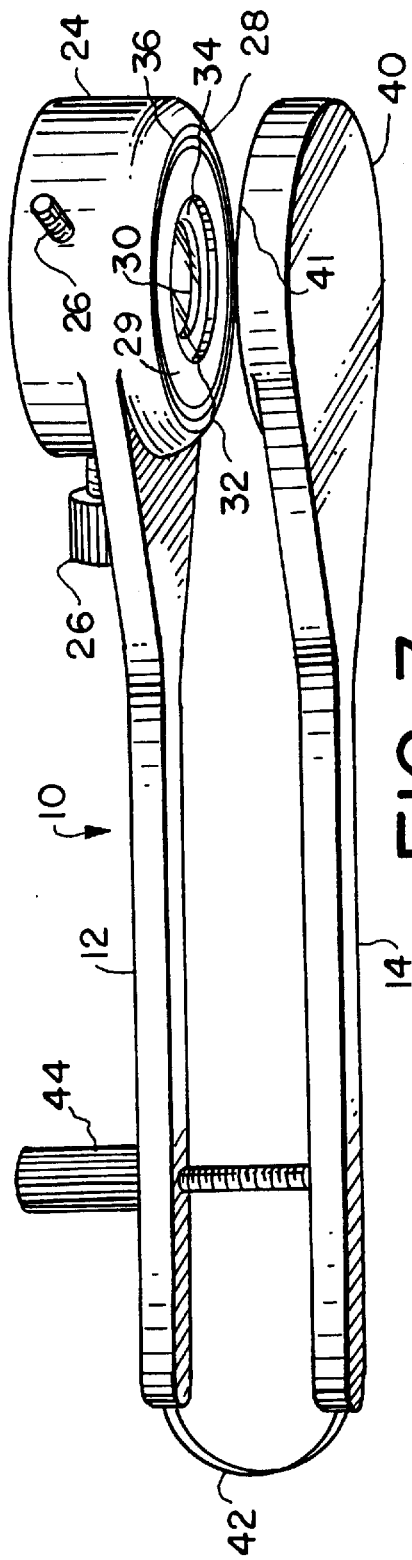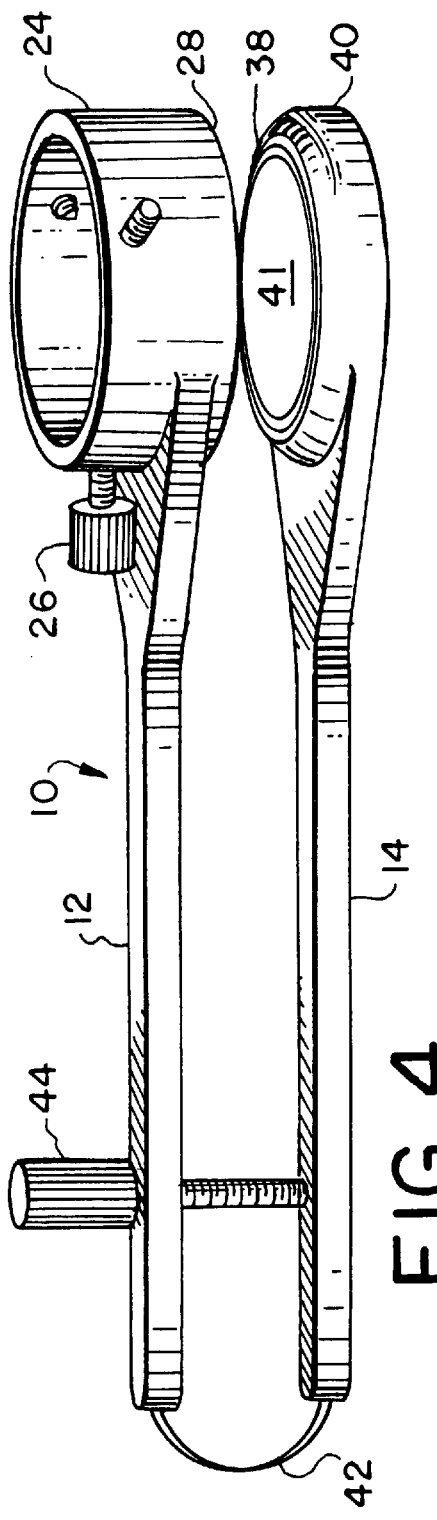

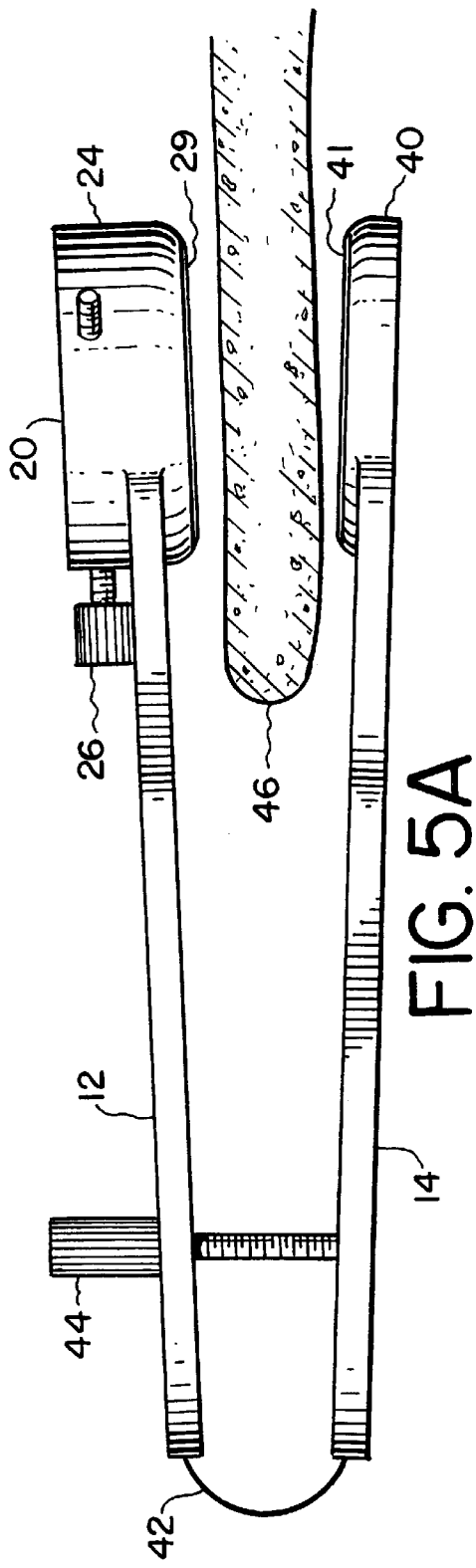
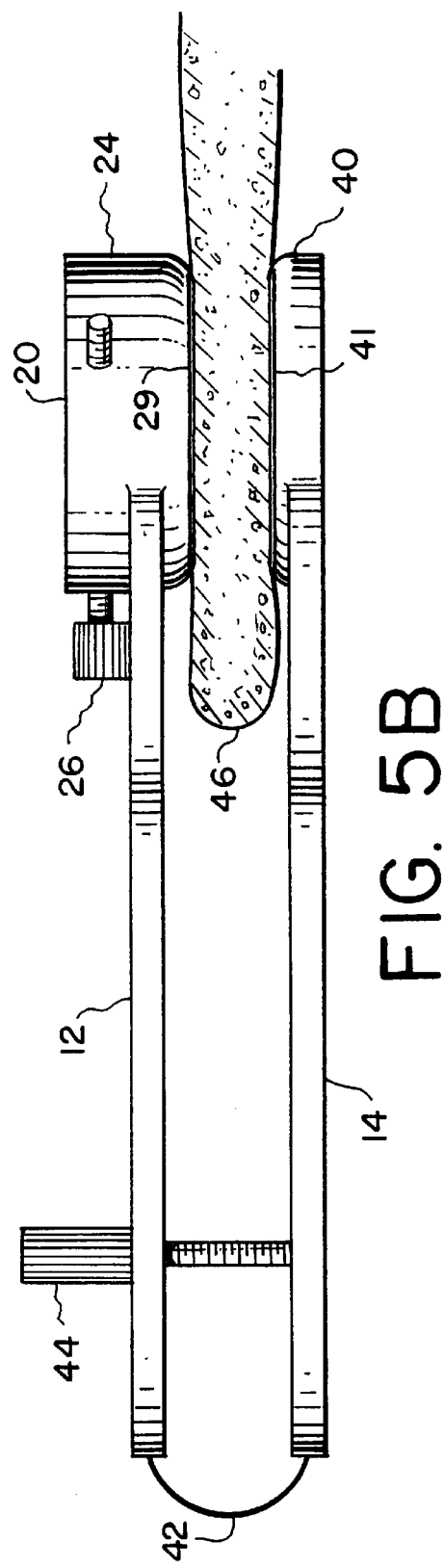
FIG. 5A
FIG. 5B

SYSTEM FOR IMAGING MECHANICALLY STABILIZED TISSUE

DESCRIPTION

This is a continuation of patent application Ser. No. 08/912,331, filed Aug. 18, 1997, now U.S. Pat. No. 5,978,695.

FIELD OF THE INVENTION

The present invention relates to an imaging system for in vivo examinations of tissues, and particularly to a confocal imaging system operative upon the tissue of a patient body part or animal subject which mechanically stabilizes the tissue to minimize instability in confocal images of the tissue. This invention is especially suitable for providing an instrument or attachment for pathological applications.

This application is related to U.S. application Ser. No. 08/683,607, filed on Jul. 15, 1996, and entitled Three-Dimensional Scanning Confocal Laser Microscope, now U.S. Pat. No. 5,880,880.

BACKGROUND OF THE INVENTION

Systems have been proposed for confocal scanning of skin, such as described in an article by Rajadhyaksha et al., entitled "In vivo Confocal Scanning Laser Microscopy of Human Skin:

Melanin provides strong contrast," The Journal of Investigative Dermatology, Volume 104, No. 6, June 1995, pages 1–7, and also Rajadhyaksha et al., entitled "Confocal laser microscope images tissue in vivo," Laser Focus World, February 1997, page 119–127. These systems have confocal optics which direct light to the patient's skin tissue and image the returned reflected light. Such optics has a limited field of view of the patient's skin tissue, which for example may cover a tissue area less than one millimeter wide. One problem with these systems is that motion of the patient during confocal imaging can cause the tissue area being imaged to move relative to the system's confocal optics, shifting the field of view of the tissue area with respect to the optics. Consequently, confocal images from such systems may appear unstable to the viewing physician, making it difficult for the physician to observe dermal structures of interest. Even slight motion of the patient's skin tissue, such as due to involuntary muscle movement in adjacent tissue or from a circulatory pulse, can cause dermal structures of a confocal image to appear to move in and out of the imaged tissue area. The confocal optics may also image other types of patient tissue in addition to dermal tissues, for example, oral tissue of the tongue or lip, but motion of such tissue can still cause instability in confocal images of tissue structures.

SUMMARY OF THE INVENTION

Accordingly, it is the principal object of the present invention to provide an improved system for confocal imaging of tissue of a patient which minimizes instability in confocal images by reducing the relative motion of the tissue with respect to the confocal imaging optics of the system.

It is another object of the present invention to provide an improved system for confocal imaging having a clamping apparatus which mechanically stabilizes the tissue to a confocal imaging system within the improved system.

Briefly described, the present invention embodies a system having a clamping apparatus with first and second members, which are spaced apart from each other. An attachment mechanism is connected to the first member for attaching the apparatus to a confocal imaging system. The attachment mechanism has a surface facing the tissue to be examined. Opposing this surface is a third member which is connected to the second member. A clamping mechanism includes the first and second members for clamping the tissue between the surface of the attachment mechanism and the surface of the third member. A window is provided in the surface of the attachment mechanism for presenting the clamped tissue to the confocal imaging system.

The clamping mechanism may include a turn screw threaded through the first and second members, or a pneumatic system, for clamping the apparatus to the tissue. An optional suction mechanism may be used to assist in clamping the tissue to the attachment mechanism.

BRIEF DESCRIPTION OF THE DRAWINGS

The foregoing objects, features and advantages of the invention will become more apparent from a reading of the following description in connection with the accompanying drawings in which:

FIG. 1 is a side elevational view of the system of the present invention showing a clamping apparatus attached to a confocal imaging system;

FIG. 2 is a top view of the clamping apparatus of FIG. 1;

FIG. 3 is a perspective view from the bottom of the clamping apparatus of FIGS. 1 and 2;

FIG. 4 is a perspective view from the top of the clamping apparatus of FIGS. 1 and 2;

FIGS. 5A and 5B are side views of the clamping apparatus of FIG. 1 showing an example of the apparatus before and after being clamped to tissue, respectively;

DETAILED DESCRIPTION OF THE INVENTION

Figure 6:
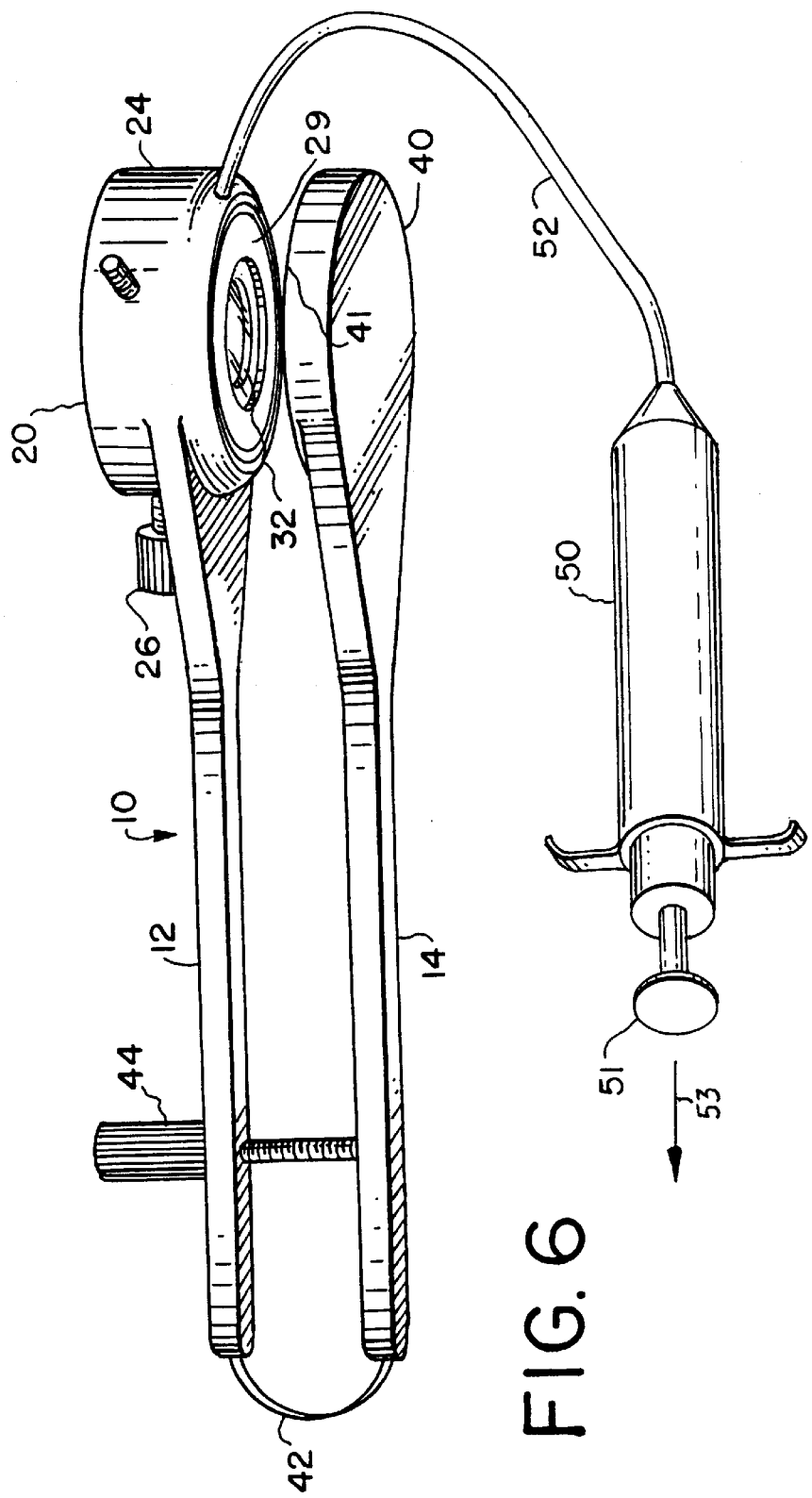
FIG. 6 is a perspective view from the bottom of the clamping apparatus of FIGS. 1 and 2 showing an optional suction mechanism to assist in clamping tissue.

Referring to FIGS. 1–4, a system 8 includes a clamping apparatus 10 having a first member 12 and a second member 14 which is spaced apart from the first member. Member 12 has a lower surface 16 opposing an upper surface 18 of member 14. At one end of member 12 is connected a mechanism 20 for attaching or coupling apparatus 10 to a confocal imaging system 22 of system 8. For purposes of illustration, confocal imaging system 22 is represented by a cylinder 23 which contains confocal optics, such as an objective focusing lens. Confocal imaging system 22 is described in related U.S. application Ser. No. 08/683,607, filed on Jul. 15, 1996. While confocal imaging is the preferred embodiment, system 22 may also represent a system using other imaging modalities, such as optical coherence tomography, described for example in Schmitt et al., "Optical characterization of disease tissues using low-coherence interferometry," Proc. of SPIE, Volume 1889 (1993), or two-photon microscopy, described for example in U.S. Pat. No. 5,034,613, to Denk et al., or deconvolution confocal microscopy, described for example in Kesterson, et al., "Confocal Microscope Capability with Desktop Affordability," Advanced Images, Oct. 1991, pages 23–24, or fluorescent imaging. The objective focusing lens in system 22 may be part of a fixed station or a portable confocal imaging system providing images of the tissue which are microscopic for pathological examination.

Mechanism 20 has an annular receptacle 24, such as a ring, having a lower member or template 28. Receptacle 24 receives cylinder 23, while pins 26, for example three, are threaded into the sides of receptacle 24, such that they can be extended into grooves or openings 27 in cylinder 23, thereby fixing the position of the confocal imaging system 22 to apparatus 10. (Openings 27 and cylinder 23 are shown in receptacle 24 of FIG. 1 as dashed lines.) Mechanism 20 is described, for example, in related Application No. 08/683,607, filed Jul. 15, 1996. Template 28 has an aperture 30 through which the confocal imaging system, i.e., confocal optics, images the tissue. Aperture 30 may, for example, be several millimeters in diameter. As best shown in FIG. 3, an annular recess 34 in the bottom surface 29 of template 28 is in communication with aperture 30, in other words, a bore of smaller to larger diameter from aperture 30 and recess 34, respectively, widens to provide an annular recess 34 at surface 29. (Recess 34 is also shown in dotted lines in FIG. 2.) In recess 34, a window 32 of a thin transparent material, such as plastic or glass, is fitted. For example, window 32 may be a thin plate of glass, suitably about 0.1–0.2 mm thick. Window 32 is sized such that it fits into annular recess 34, however, window 32 may be square in shape, thus requiring grooves in recess 34 to receive the corners of the window. Window 32, for example, may be a coverslip as conventionally used in preparation of slides for a typical optical microscope. Surface 29 of template 28 has a textured surface, which is represented by raised ridges 36.

In apparatus 10, an opposing member 40 has an upper surface 41 which opposes surface 29 of mechanism 20. Opposing member 40 is connected to an end 14b of member 14. Upper surface 41 has a textured surface, which is represented by raised ridges 38 (see FIG. 4). Surface 41 optionally may have a layer of deformable compliant material, such as urethane. Member 40 may be a disk, as illustrated in the figures, however the shape of member 40 may depend on the patient body part having the tissue to be located between surfaces 29 and 41. For example, member 40 may be split into two or more sections, like a fork, to avoid interfering with other tissue near the body part, such as when the tissue to be imaged is in the middle of the tongue. Other shapes for member 40 may also be used, such as oblong or rectangle. Accordingly, member 40 may be any structure providing a surface 41 which opposes surface 29 and can provide pressure and traction against a patient body part clamped between surfaces 29 and 41, as described below. Members 12 and 14, receptacle 24, and member 40 may be made of stainless-steel or plastic. Receptacle 24 may be a separate component that is joined (screwed or welded) to the assembly of member 12.

A clamping mechanism in apparatus 10 clamps tissue in the space between surface 29 of mechanism 20 and surface 41 of member 40. The clamping mechanism includes a hinge provided by a spring 42 to members 12 and 14 at the ends thereof opposite mechanism 20 and member 40, respectively, a turn screw 44 threaded in holes 12a and 14a through members 12 and 14, respectively, and members 12 and 14 connected to mechanism 20 and member 40, respectively. Spring 42 is a flat strip of flexible material (steel, plastic or bronze), and applies a force on members 12 and 14 pushing the members apart from each other. Screw 44 is rotatable to manually adjust the spacing between surfaces 29 and 41, such that tissue can be clamped between surfaces 29 and 41, and released therefrom. Alternatively, the clamping mechanism may be provided by two or more screws, similar to screw 44, threaded through members 12 and 14 for setting the space between surfaces 29 and 41. These screws can be independently adjusted to provide angular adjustment of members 12 and 14 to each other to insure that surfaces 29 and 41 are parallel as they restrain the tissue. Other means for clamping may also be used which are similar to clamps of conventional surgical instruments.

Referring to the example shown in FIGS. 5A and 5B, a tongue 46 having the tissue of a patient to be examined is first inserted between members 12 and 14. To facilitate insertion of tongue 46, an operator turns screw 44 until the space between surfaces 29 and 41 is wider than the thickness of the tongue. With tongue 46 between surfaces 29 and 41 and the area of the tongue to be investigated facing window 32, the tongue is clamped to apparatus 10 by the operator turning screw 44 until the tongue is immobilized with respect to surfaces 29 and 41 without damaging the tissue or causing unnecessary discomfort to the patient. The textured surfaces of surfaces 29 and 41 provide traction against the surfaces of tongue 46 to maintain the tissue area under investigation stable for imaging. When apparatus 10 is clamped to tongue 46, surfaces 29 and 41 of mechanism 20 and member 40, respectively, are substantially parallel to each other. Accordingly, the downward clamping force of mechanism 20 is substantially parallel to the upward clamping force of member 40 against the surfaces of tongue 46. This is an important feature of the invention since it avoids the tongue from squeezing out of clamping apparatus 10.

The confocal imaging system 22 is attached into receptacle 24 of mechanism 20 using pins 26, as shown in FIG. 1, to provide an integrated assembly of the imaging system 22 and apparatus 10. The attachment may be done most conveniently after the tissue is clamped by apparatus 10, however it may occur before tongue 46 is clamped. Window 32 in surface 29 of mechanism 20 presents a tissue area of the clamped tongue to the confocal imaging optics in system 22, thereby enabling confocal imaging of the tissue beneath the window. The tissue under the window is thus mechanical stabilized to the confocal imaging system 22, which minimize instability in confocal images by reducing the relative motion of tissue with respect to the confocal imaging optics of system 22. Apparatus 10 may also operate without window 32, such that window 32 is removed from recess 34 prior to apparatus 10 being clamped to tissue.

Optionally, a suction mechanism may assist in clamping apparatus 10 to tongue 46, as shown in FIG. 6. The suction mechanism includes a syringe 50 connected through a hose 52 to receptacle 24. An annular opening, or one or more holes, provided in surface 29 of receptacle 24 is in communication with hose 52, such that after apparatus 10 is clamped to tongue 46, pulling plunger 51 of syringe 50 in the direction of arrow 53 suctions any air between surface 29 and the surface of tongue 46 facing surface 29. This results in a vacuum adhering surface 29 and the clamped tissue together, thereby further stabilizing the tongue against window 32.

Figure 7A:
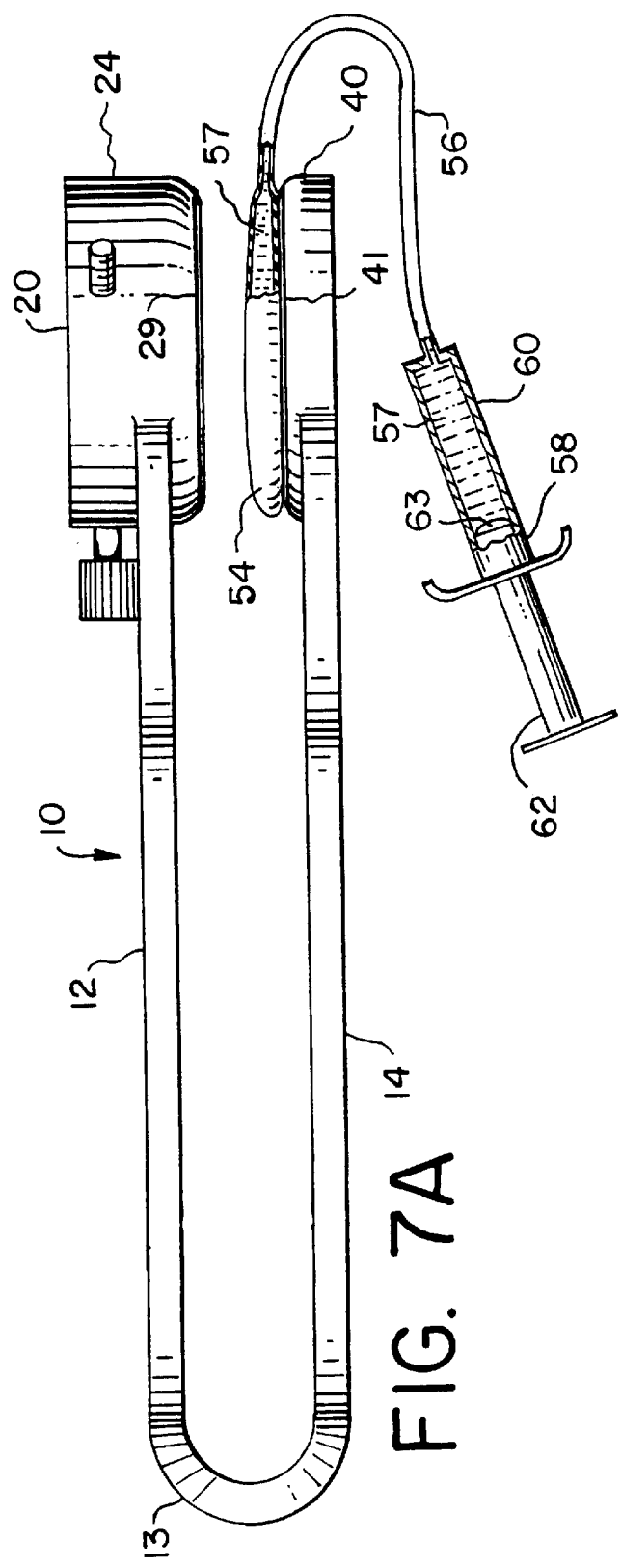
FIGS. 7A and 7B are side views of the clamping apparatus similar to FIG. 1 showing a clamping mechanism with a pneumatic system before and after the bladder of the pneumatic system is inflated, respectively, to clamp the apparatus to tissue.
Figure 7B:
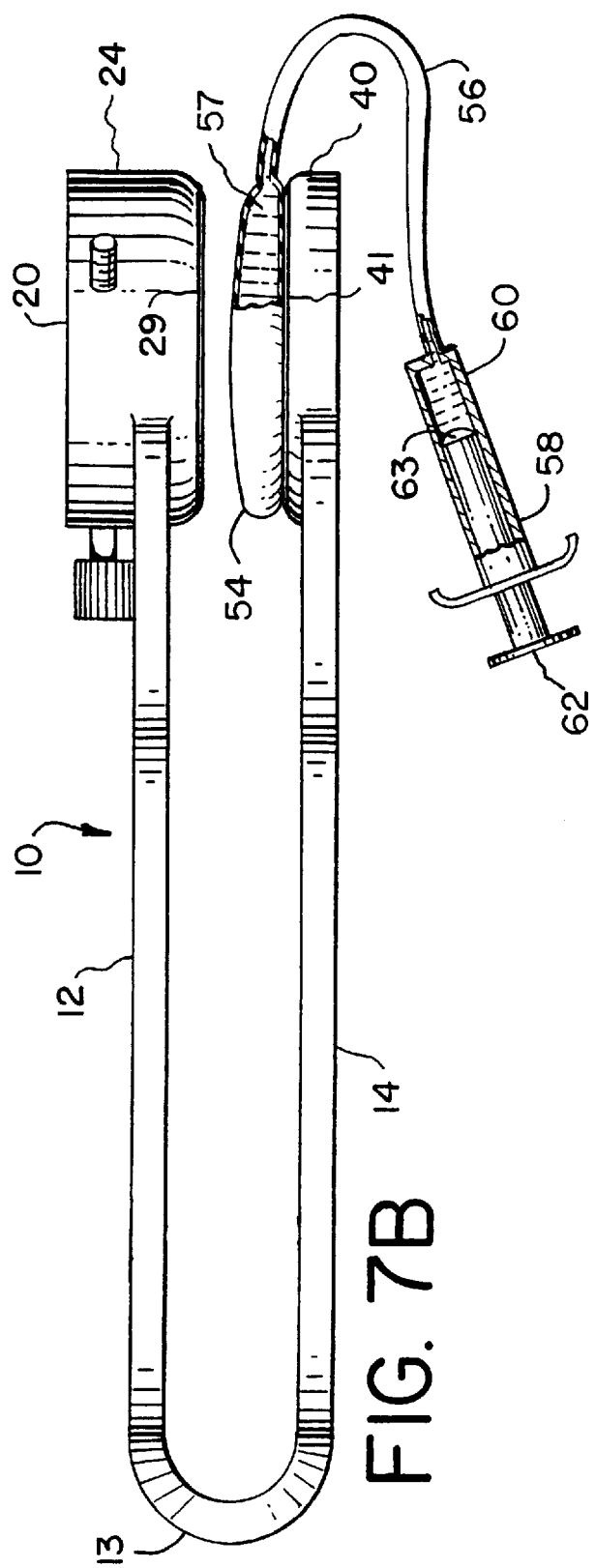

Referring to FIGS. 7A and 7B, clamping apparatus 10 is shown in which the clamping mechanism is provided by a pneumatic system instead of turn screw 44 (FIG. 1), and members 12 and 14 are part of a single C-shaped member 13 without hinge 42. The pneumatic system includes a bladder 54, which is attached to surface 41, a syringe 58, and a hose 56 connecting syringe 58 to bladder 54. A fluid 57, such as air, water, or the like, can pass through hose 56 between bladder 54 and a cavity 60 in syringe 58. Cavity 60 is defined by the interior of syringe 58 and the head 63 of a plunger 62 in syringe 58. Plunger 62 is slidable within syringe 58 to change the volume of fluid 57 in both cavity 60 and bladder 54.

As shown in FIG. 7A, when plunger 62 is in a first position, bladder 54 is deflated due to the lack of fluid 57 in bladder 54. In this first position, the tissue, such as tongue 46 of FIG. 5A, may be inserted between mechanism 20 and member 40. Once the tissue is properly positioned under mechanism 20, plunger 62 is pushed by an operator to a second position, as shown in FIG. 7B. This forces some of the fluid 57 in cavity 60 through hose 56 into bladder 54, which causes bladder 54 to inflate and force the tissue against surface 29. Bladder 54 is inflated to sufficiently clamp apparatus 10 to the tissue. Hose 56 may be clamped if needed to prevent back flow of fluid 57 into cavity 60 of syringe 58. Optionally, single or multiple turn screws 44 (FIG. 1) may be used in apparatus 10 in combination with the pneumatic system in which bladder 54, when inflated, provides an additional clamping force upon the tissue.

System 8 is particularly useful for mechanically stabilizing the confocal imaging system 22 to oral tissue, such as the tongue or lip, which may have mucus on its surface. However, apparatus 10 may be sized to accommodate clamping of other tissues of the patient to mechanism 20, such as fingers, the palm of a hand, nails, ears, or male genitalia.

Figure 8A:
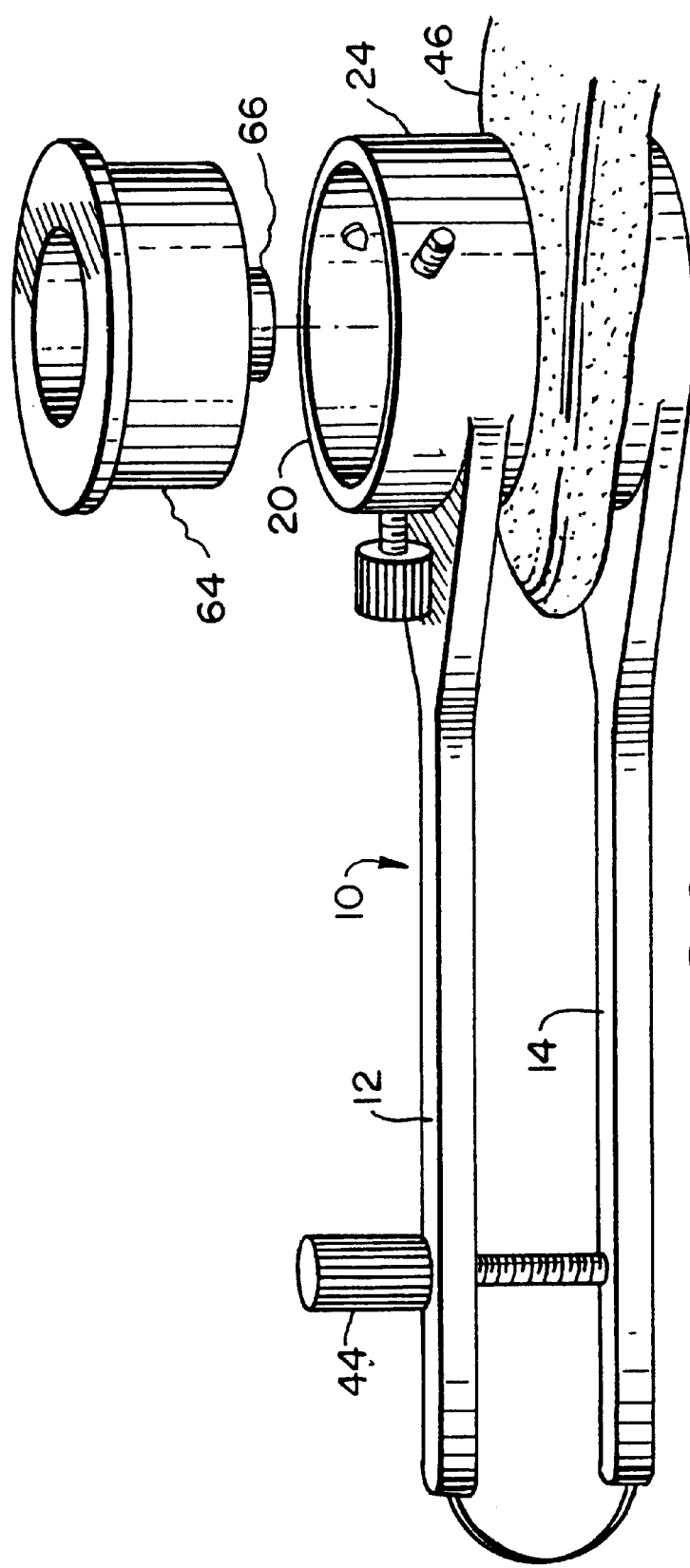
FIGS. 8A, 8B and 8C are perspective views from the top of the clamping apparatus of FIG. 5B showing a biopsy device before, during and after taking a biopsy of the clamped tissue through the apparatus, respectively.
Figure 8B:
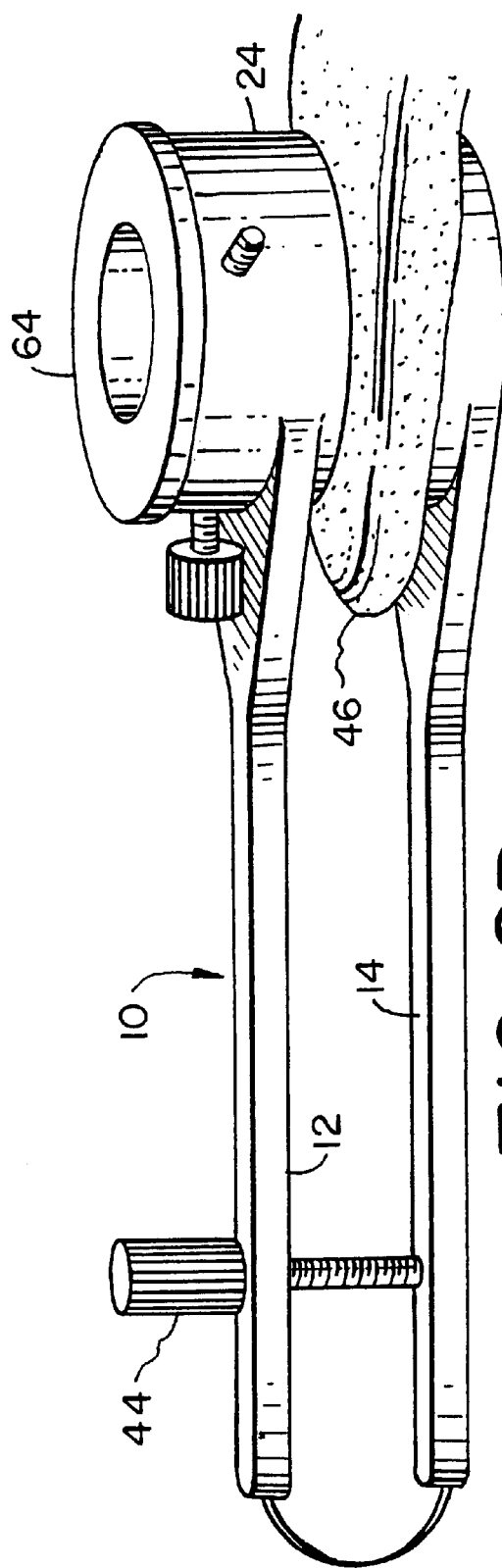
Figure 8C:
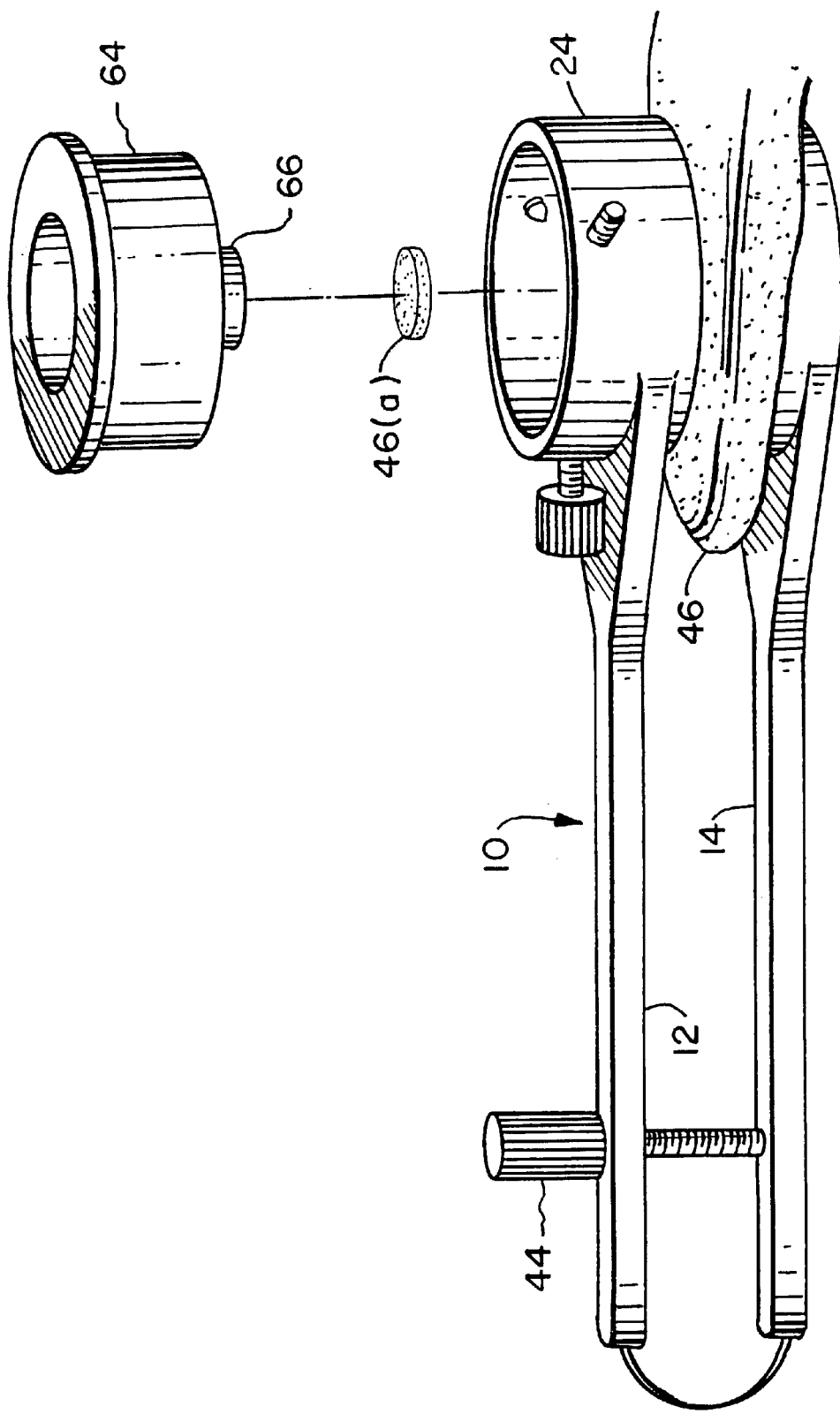

After imaging by confocal system 22, the tissue is released from apparatus 10 by turning turn screw 44 (FIG. 1) in a direction which moves member 40 and mechanism 20 apart from each other, or if the pneumatic system of FIGS. 7A and 7B is used, the tissue is released by pulling plunger 62 back to its first position to deflate bladder 54. However, before the tissue is released from apparatus 10, a biopsy device 64 can be inserted into receptacle 24 to take a biopsy 46(a) of the tissue under window 32, as shown in FIGS. 8A–8C. The biopsy device 64 has a projection 66 which, when positioned in receptacle 24 (FIG. 8B), cuts through window 32 and into the tissue under window 32. However, window 32 may be removed from recess 34 prior to the clamping of apparatus 10 to tissue, such that biopsy device 64 will not need to cut window 32. Blade(s) (not shown) in projection 66 are then extended to cut beneath the tissue surface. As device 64 is removed from receptacle 24 (FIG. 8C) an excised biopsy 46(a) is provided. This biopsy can then be examined by typical pathological techniques to confirm any tissue abnormalities found during imaging of the tissue.

From the foregoing description, it will be apparent that there has been provided an improved system for confocal imaging in tissue. Variations and modifications in the herein described system in accordance with the invention will undoubted suggest themselves to those skilled in the art. For example, members 12 and 14, tissue engaging parts 20 and 40, and even spring 42, may be an integrated body molded from plastic or stainless steel. Accordingly, the foregoing description should be taken as illustrative and not in a limiting sense.

What is claimed is:

1. A system for imaging mechanically stabilized tissue comprising:

means for clamping the tissue by application of force to said tissue; and an imaging system for imaging at least a portion of the clamped tissue attached to said clamping means, wherein said imaging system has optics for directing light into said clamped tissue in which said same optics receives returned reflected light from the clamped tissue representing microscopic images of the tissue.

2. The system according to claim 1 wherein said clamping means comprises:

a first member and a second member spaced apart and opposing said first member; and means coupled to said first member for attaching said first member to said imaging system.

3. The system according to claim 1 wherein said clamping means provides an aperture through which said optics of said imaging system directs and receives light.

4. A method for mechanically stabilizing tissue to an imaging system comprising the steps of:

clamping the tissue by application of force to said tissue;

attaching the imaging system to the clamped tissue to present a limited view of an area of the clamped tissue; and producing one or more images of said clamped tissue by returned reflected light.

5. The method according to claim 4 wherein said producing step is carried out with the aid of a confocal microscope.

6. The method according to claim 4 wherein said producing step is carried out in accordance with one of two-photo microscopy and optical coherence tomography.

7. The method according to claim 6 wherein said attaching step is carried out after said clamping step.

8. The method according to claim 4 wherein said attaching step is carried out before said clamping step.

* * * * *